US006080190A

United States Patent [19]
Schwartz

[11] Patent Number: 6,080,190
[45] Date of Patent: *Jun. 27, 2000

[54] INTRALUMINAL STENT

[75] Inventor: Robert S. Schwartz, Rochester, Minn.

[73] Assignee: Medtronic, Inc., Minneapolis, Minn.

[ * ] Notice: This patent is subject to a terminal disclaimer.

[21] Appl. No.: 09/069,387

[22] Filed: Apr. 29, 1998

Related U.S. Application Data

[60] Continuation of application No. 08/429,977, Apr. 27, 1995, Pat. No. 5,800,507, which is a division of application No. 08/079,222, Jun. 17, 1993, which is a continuation of application No. 07/854,118, Mar. 19, 1992, abandoned.

[51] Int. Cl.$^7$ .................................................. A61F 2/06
[52] U.S. Cl. .................................. 623/1; 623/11; 623/12; 604/8; 604/104; 600/36; 606/191; 606/151; 606/194; 606/195
[58] Field of Search .................................... 623/1, 11, 12; 606/191–200, 151–158; 600/36; 604/8, 104

[56] References Cited

U.S. PATENT DOCUMENTS

| | | |
|---|---|---|
| 4,193,138 | 3/1980 | Okita . |
| 4,208,745 | 6/1980 | Okita . |
| 4,229,838 | 10/1980 | Mano . |
| 4,548,736 | 10/1985 | Muller et al. . |
| 4,768,507 | 9/1988 | Fischell et al. . |
| 4,886,062 | 12/1989 | Wiktor . |
| 4,897,269 | 1/1990 | Mezei . |
| 5,092,841 | 3/1992 | Spears . |
| 5,246,451 | 9/1993 | Trescony et al. . |
| 5,298,255 | 3/1994 | Sawwamoto et al. . |
| 5,413,601 | 5/1995 | Keshelava . |
| 5,800,507 | 9/1998 | Schwartz ..................................... 623/1 |

FOREIGN PATENT DOCUMENTS

| | | |
|---|---|---|
| 0364787 | 4/1990 | European Pat. Off. . |
| 0366564 | 5/1990 | European Pat. Off. . |
| 9013332 | 11/1990 | WIPO . |
| 9112779 | 9/1991 | WIPO . |
| 9222312 | 12/1992 | WIPO . |

OTHER PUBLICATIONS

"Bioartifical Polymeric Materials Obtained from Blends of Synthetic Polymers with Fibrin and Collagen", by G. Soldani et al, pub. The International Journal of Artificial Organs, vol. 14/No. 5, 1991, pp. 295–303.

"New Biolized Polymers for Cardiovascular Applications" by P. Giusti et al, pub. Life Support Syst. 1986, vol. 3, No. (Suppl. 1) Proc. Erv. Soc. Artif. Organs Ann. Meet. 12th. 1985.

"Evaluation of Fibrin Seal in Animal Experiments" by A. Haverich et al, pub. in Torac Cardiovasc. Surgeon 30 (1982) pp. 215–222.

"Use of Fibrin Film as a Carrier for Drug Delivery: In Vitro Drug Permeabilities of Fibrin Film" by Shozo Miyazaki et al, pub. in Chem. Pharm. Bull. 28(7), 1980, pp. 2261–2264.

"Initial Experience with Percutaneous Implanted Exogenous Fibrin Sleeves in Porcine Coronary Arteries" by Holms D.R. et al, in submitted for publication in Circulation, Dec. 15, 1992.

"A Cascade Model for Restenosis. A Special Case of Atherosclerosis Progression" by P. Libby et al in Circulation 86(6) 11147–52, Dec. 1992.

"A Practical Proliferative Model in Porcine Coronary Arteries" by Robert S. Schwartz et al in Circulation 82(6):2190–2200, Dec. 1990.

(List continued on next page.)

*Primary Examiner*—David H. Willse
*Assistant Examiner*—Choon P. Koh

[57] ABSTRACT

An intraluminal stent comprising fibrin is capable of reducing the incidence of restenosis at the site of vascular injury such as that produced by an angioplasty procedure.

29 Claims, 3 Drawing Sheets

OTHER PUBLICATIONS

"Restenosis and the Proportional Neointimal Response to Coronary Arty Injury: Results in Porcine Model" by Robert S. Schartz et al, J.AM Coll. Cardiol., 19:267–74, Feb. 1992.

"The Restenosis Paradigm Revisited: An Alternative Proposal for Cellular Mechanisms" [editorial], by Schwartz et al, in J. AM Coll.Cardiol. 20(5) 1284–93, Nov. 1992.

"Percutaneous Polymeric Stents in Porcine Coronary Arteries. Initial Experience with Polyethylene Terephthalate Stents", by Murphy R.G. et al. in Circulation, 86(5) 1596–604 Nov. 1992.

"Polymeric Stenting in the Porcine Coronary Artery Model: Differential Outcome of Exogenous Fibrin Sleeves Versus Polyurethane Coated Stents", Holms Jr. et al, JACC vol. 24, No.2, Aug. 1994:525–31, Experimental Studies, pp. 525–531.

"Marked Inflammatory Sequelae to Implantation of Biodegradable and Nonbiodegradable Polymers in Porcine Coronary Arteries", van der Giessen et al, Circulation 94(7) 1690–97, Oct. 1996.

INTRALUMINAL STENT

This application is a continuation of application Ser. No. 08/429,977 filed Apr. 27,1995, U.S. Pat. No. 5,800,507 which is a divisional application of application Ser. No. 08/079,222 filed Jun. 17, 1993 which is a continuation of application Ser. No. 07/854,118 filed Mar. 19,1992, now abandoned.

BACKGROUND OF THE INVENTION

This invention relates to a method for lessening restenosis of body lumens and to intraluminal stents having anti-thrombosis and anti-restenosis properties.

Restenosis is the closure of a peripheral or coronary artery following trauma to the artery caused by efforts to open an occluded portion of the artery, such as, for example, by dilation, ablation, atherectomy or laser treatment of the artery. For these angioplasty procedures, restenosis occurs at a rate of about 20–50% depending on the vessel location, lesion length and a number of other variables. Restenosis is believed to be a natural healing reaction to the injury of the arterial wall that is caused by angioplasty procedures. The healing reaction begins with the clotting of blood at the site of the injury. The final result of the complex steps of the healing process is intimal hyperplasia, the migration and proliferation of medial smooth muscle cells, until the artery is again stenotic or occluded.

In an attempt to prevent restenosis, metallic intravascular stents have been permanently implanted in coronary or peripheral vessels. The stent is typically inserted by catheter into a vascular lumen and expanded into contact with the diseased portion of the arterial wall, thereby providing internal support for the lumen. However, it has been found that restenosis can still occur with such stents in place. Also, the stent itself can cause undesirable local thrombosis. To address the problem of thrombosis, persons receiving stents also receive extensive systemic treatment with anticoagulant and antiplatelet drugs.

To address the restenosis problem, it has been proposed to provide stents which are seeded with endothelial cells (Dichek, D. A. et al Seeding of Intravascular Stents With Genetically Engineered Endothelial Cells; Circulation 1989; 80: 1347–1353). In that experiment, sheep endothelial cells that had undergone retrovirus-mediated gene transfer for either bacterial beta-galactosidase or human tissue-type plasmogen activator were seeded onto stainless steel stents and grown until the stents were covered. The cells were therefore able to be delivered to the vascular wall where they could provide therapeutic proteins. Other methods of providing therapeutic substances to the vascular wall by means of stents have also been proposed such as in international patent application WO 91/12779 "Intraluminal Drug Eluting Prosthesis" and international patent application WO 90/13332 "Stent With Sustained Drug Delivery". In those applications, it is suggested that antiplatelet agents, anticoagulant agents, antimicrobial agents, antimetabolic agents and other drugs could be supplied in stents to reduce the incidence of restenosis.

In the vascular graft art, it has been noted that fibrin can be used to produce a biocompatible surface. For example, in an article by Soldani et al., "Bioartificial Polymeric Materials Obtained from Blends of Synthetic Polymers with Fibrin and Collagen" International Journal of Artificial Organs, Vol. 14, No. 5, 1991, polyurethane is combined with fibrinogen and cross-linked with thrombin and then made into vascular grafts. In vivo tests of the vascular grafts reported in the article indicated that the fibrin facilitated tissue ingrowth and was rapidly degraded and reabsorbed. Also, in published European Patent Application 0366564 applied for by Terumo Kabushiki Kaisha, Tokyo, Japan, discloses a medical device such as an artificial blood vessel, catheter or artificial internal organ is made from a polymerized protein such as fibrin. The fibrin is said to be highly nonthrombogenic and tissue compatible and promotes the uniform propagation of cells that regenerates the intima. Also, in an article by Gusti et al., "New Biolized Polymers for Cardiovascular Applications", Life Support Systems, Vol. 3, Suppl. 1, 1986, "biolized" polymers were made by mixing synthetic polymers with fibrinogen and cross-linking them with thrombin to improve tissue ingrowth and neointima formation as the fibrin biodegrades. Also, in an article by Haverich et al., "Evaluation of Fibrin Seal in Animal Experiments", Thoracic Cardiovascular Surgeon, Vol. 30, No. 4, pp. 215–22, 1982, the authors report the successful sealing of vascular grafts with fibrin. However, none of these teach that the problem of restenosis could be addressed by the use of fibrin and, in fact, conventional treatment with anticoagulant drugs following angioplasty procedures is undertaken because the formation of blood clots (which include fibrin) at the site of treatment is thought to be undesirable.

SUMMARY OF THE INVENTION

I have found that an intraluminal stent comprising fibrin is capable of reducing the incidence of restenosis at the site of a vascular injury and can also serve as a matrix for the local administration of drugs to the site of a vascular injury. Fibrin is a naturally occurring bioabsorbable polymer of fibrinogen that arises during blood coagulation. As set forth above, antiplatelet and anticoagulant agents are thought to be desirable to prevent thrombosis (and to thereby prevent fibrin formation) in the lumen at the site of dilation or other treatment. By contrast, I have found that providing fibrin at the site of treatment can provide a readily tolerated, bioabsorbable surface which will interact in a natural manner with the body's healing mechanism and reduce the prospect for the intimal hyperplasia that causes restenosis.

A stent according to the present invention can be made in virtually any configuration and can be delivered conventionally by catheter to the site of the luminal closure or restriction. A method for making such a stent and a method for treating restenosis with fibrin is also disclosed.

BRIEF DESCRIPTION OF THE DRAWINGS

FIG. 4 is an elevational view of a stent and rigid tube into which the stent is inserted. FIG. 5 is an elevational view of the tube of FIG. 4 into which a catheter balloon is inserted. FIG. 6 is partial sectional view of the tube of FIG. 5 with included stent and catheter. FIG. 7 is a partial sectional view of the tube of FIG. 6 to which fibrin has been added. FIG. 8 is a partial sectional view of the tube of FIG. 7 in which the balloon has been expanded. FIG. 9 is an elevational view of the resulting stent being removed from the tube of FIG. 8. FIG. 10 is an elevational view of the completed stent mounted on the balloon of a catheter.

DETAILED DESCRIPTION OF THE INVENTION

Figure 1:
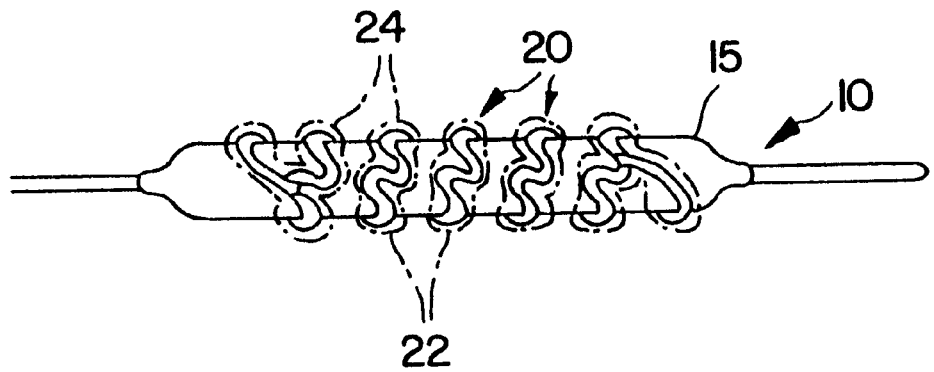
FIG. 1 is a elevational view of a balloon catheter with a metallic stent including a fibrin coating according to the present invention.

The present invention provides a stent comprising fibrin. The term "fibrin" herein means the naturally occurring polymer of fibrinogen that arises during blood coagulation.

Blood coagulation generally requires the participation of several plasma protein coagulation factors: factors XII, XI, IX, X, VIII, VII, V, XIII, prothrombin, and fibrinogen, in addition to tissue factor (factor III), kallikrein, high molecular weight kininogen, $Ca^{+2}$, and phospholipid. The final event is the formation of an insoluble, cross-linked polymer, fibrin, generated by the action of thrombin on fibrinogen. Fibrinogen has three pairs of polypeptide chains (ALPHA 2-BETA 2-GAMMA 2) covalently linked by disulfide bonds with a total molecular weight of about 340,000. Fibrinogen is converted to fibrin through proteolysis by thrombin. An activation peptide, fibrinopeptide A (human) is cleaved from the amino-terminus of each ALPHA chain; fibrinopeptide B (human) from the amino-terminus of each BETA chain. The resulting monomer spontaneously polymerizes to a fibrin gel. Further stabilization of the fibrin polymer to an insoluble, mechanically strong form, requires cross-linking by factor XIII. Factor XIII is converted to XIIIa by thrombin. XIIIa cross-links the GAMMA chains of fibrin by transglutaminase activity, forming EPSILON-(GAMMA-glutamyl) lysine cross-links. The ALPHA chains of fibrin also may be cross-linked.

Since fibrin blood clots are naturally subject to fibrinolysis as part of the body's repair mechanism, implanted fibrin can be rapidly biodegraded. Plasminogen is a circulating plasma protein that is adsorbed onto the surface of the fibrin polymer. The adsorbed plasminogen is converted to plasmin by plasmogen activator released from the vascular endothelium. The plasmin will then break down the fibrin into a collection of soluble peptide fragments.

Methods for making fibrin and forming it into implantable devices are well known as set forth in the following patents and published applications which are hereby incorporated by reference. In U.S. Pat. No. 4,548,736 issued to Muller et al., fibrin is clotted by contacting fibrinogen with a fibrinogen-coagulating protein such as thrombin, reptilase or ancrod. Preferably, the fibrin in the fibrin-containing stent of the present invention has Factor XIII and calcium present during clotting, as described in U.S. Pat. No. 3,523,807 issued to Gerendas, or as described in published European Patent Application 0366564, in order to improve the mechanical properties and biostability of the implanted device. Also preferably, the fibrinogen and thrombin used to make fibrin in the present invention are from the same animal or human-species as that in which the stent of the present invention will be implanted in order to avoid cross-species autoimmune reactions. In the Muller patent, the fibrin product is in the form of a fine fibrin film produced by casting the combined fibrinogen and thrombin in a film and then removing moisture from the film osmotically through a moisture permeable membrane. In the European Patent Application 0366564, a substrate (preferably having high porosity or high affinity for either thrombin or fibrinogen) is contacted with a fibrinogen solution and with a thrombin solution. The result is a fibrin layer formed by polymerization of fibrinogen on the surface of the device. Multiple layers of fibrin applied by this method could provide a fibrin layer of any desired thickness. Or, as in the Gerendas patent, the fibrin can first be clotted and then ground into a powder which is mixed with water and stamped into a desired shape in a heated mold. Increased stability can also be achieved in the shaped fibrin by contacting the fibrin with a fixing agent such as glutaraldehyde or formaldehyde. These and other methods known by those skilled in the art for making and forming fibrin may be used in the present invention.

Preferably the coagulating effect of any residual coagulation protein in the fibrin should be neutralized before employing it in the stent of the present invention in order to prevent clotting at the fibrin interface with blood after stent implantation. This can be accomplished, for example, by treating the fibrin with irreversible coagulation inhibitor compounds after polymerization. For example, hirudin or D-phenylalanyl-propyl-arginine chloromethyl ketone (PPACK) could be used. Anti-coagulants such as heparin can also be added to reduce the possibility of further coagulation.

Polymeric materials can also be intermixed in a blend or co-polymer with the fibrin to produce a material with the desired properties of fibrin with improved structural strength. For example, the polyurethane material described in the article by Soldani et al., "Bioartificial Polymeric Materials Obtained from Blends of Synthetic Polymers with Fibrin and Collagen" International Journal of Artificial Organs, Vol. 14, No. 5, 1991, which is incorporated herein by reference, could be sprayed onto a suitable stent structure. Suitable polymers could also be biogradeable polymers such as polyphosphate ester, polyhydroxybutyric valerate (PHBV) and the like.

In U.S. Pat. No. 4,548,736 issued to Muller et al., a fibrin composition is disclosed which can be a bioabsorbable matrix for delivery of drugs to a patient. Such a fibrin composition can also be used in the present invention by incorporating a drug or other therapeutic substance useful in diagnosis or treatment of body lumens to the fibrin provided on the stent. The drug, fibrin and stent can then be delivered to the portion of the body lumen to be treated where the drug may elute to affect the course of restenosis in surrounding luminal tissue. Examples of drugs that are thought to be useful in the treatment of restenosis are disclosed in published international patent application WO 91/12779 "Intraluminal Drug Eluting Prosthesis" which is incorporated herein by reference. Therefore, useful drugs for treatment of restenosis and drugs that can be incorporated in the fibrin and used in the present invention can include drugs such as anticoagulant drugs, antiplatelet drugs, antimetabolite drugs, anti-inflammatory drugs and antimitotic drugs. Such therapeutic substances can also be icroencapsulated prior to their inclusion in the fibrin. The micro-capsules then control the rate at which the therapeutic substance is provided to the blood stream or the body lumen. This avoids the necessity for dehydrating the fibrin as set forth in Muller et al., since a dense fibrin structure would not be required to contain the therapeutic substance and limit the rate of delivery from the fibrin. For example, a suitable fibrin matrix for drug delivery can be made by adjusting the pH of the fibrinogen to below about pH 6.7 in a saline solution to prevent precipitation (e.g., NaCl, CaCl, etc.), adding the microcapsules, treating the fibrinogen with thrombin and mechanically compressing the resulting fibrin into a thin film. The microcapsules which are suitable for use in this invention are well known. For example, the disclosures of U.S. Pat. No. 4,897,268; 4,675,189; 4,542,025; 4,530,840; 4,389,330; 4,622,244; 4,464,317; and 4,943,449 could be used and are incorporated herein by reference.

Figure 2:
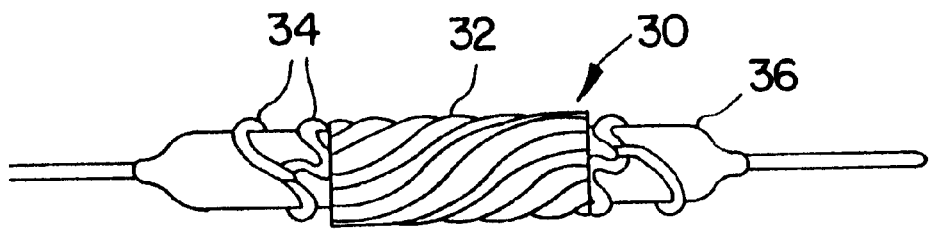
FIG. 2 is a elevational view of a balloon catheter with a metallic stent including a fibrin film according to the present invention.

The term "stent" herein means any device which when placed into contact with a site in the wall of a lumen to be treated, will also place fibrin at the lumen wall and retain it at the lumen wall. This can include especially devices delivered percutaneously to treat coronary artery occlusions and to seal dissections or aneurysms of splenic, carotid, iliac and popliteal vessels. The stent can also have underlying polymeric or metallic structural elements onto which the fibrin is applied or the stent can be a composite of fibrin intermixed with a polymer. For example, a deformable metal wire stent such as that disclosed in U.S. Pat. No. 4,886,062 issued to Wiktor could be coated with fibrin as set forth above in one or more coats (i.e polymerization of fibrin on the metal framework by application of a fibrinogen solution and a solution of a fibrinogen-coagulating protein) or provided with an attached fibrin preform such as an encircling film of fibrin made as set forth above (i.e a cast film as set forth in the Muller et al. patent). The stent and fibrin could then be placed onto the balloon at a distal end of a balloon catheter and delivered by conventional percutaneous means (e.g. as in an angioplasty procedure) to the site of the restriction or closure to be treated where it would then be-expanded into contact with the body lumen by inflating the balloon. The catheter can then be withdrawn, leaving the fibrin stent of the present invention in place at the treatment site. The stent may therefore provide both a supporting structure for the lumen at the site of treatment and also a structure supporting the secure placement of fibrin at the lumen wall. FIG. 1 shows a stent having this general construction in place on a balloon catheter. A catheter 10 has a balloon 15 upon which a stent 20 has been placed, the stent 20 having a deformable metal portion 22 and a fibrin coating 24 thereon. FIG. 2 shows an alternative stent 30 in which a fibrin film 32 has been affixed to the underlying metallic framework 34 by affixing it to the stent 30 by e.g. wrapping the film 32 around the framework 34 and securing the film 32 to the framework 34 (e.g. with an adhesive material) so that the film 32 will stay on the balloon 36 and framework 34 until it is delivered to the site of treatment. The film 32 is preferably wrapped over the framework 34 with folds or wrinkles that will allow the stent 30 to be readily expanded into contact with the wall of the lumen to be treated.

Figure 3:
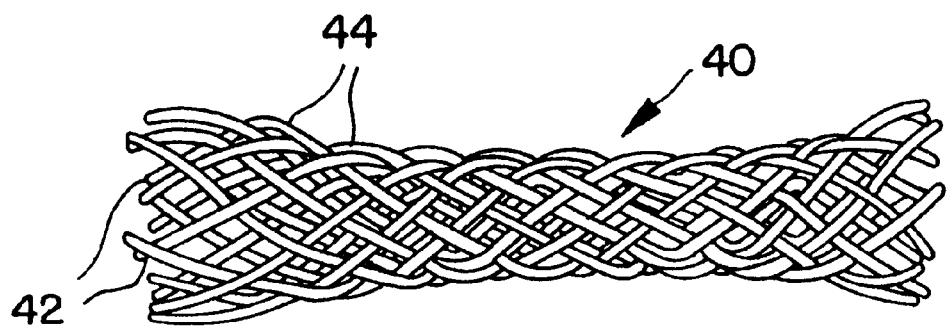
FIG. 3 is an elevational view of a polymeric stent incorporating fibrin according to the present invention.
Figure 4:
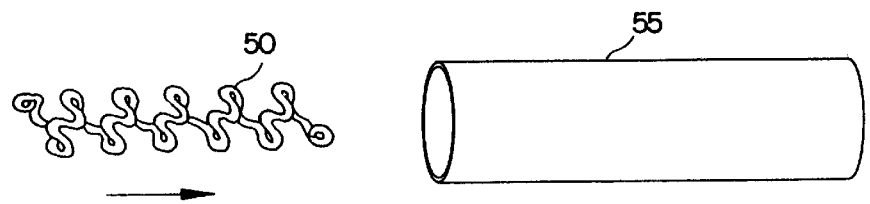
FIGS. 4–10 illustrate a method of making a stent according to the present invention.
Figure 5:
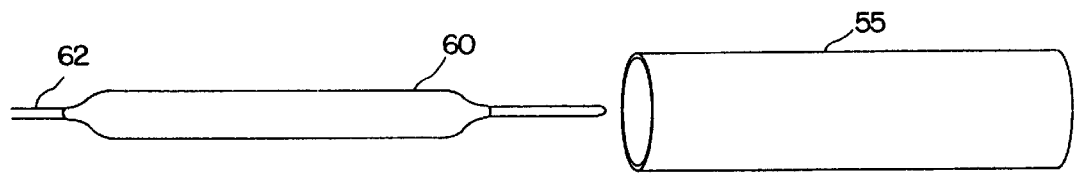
Figure 6:
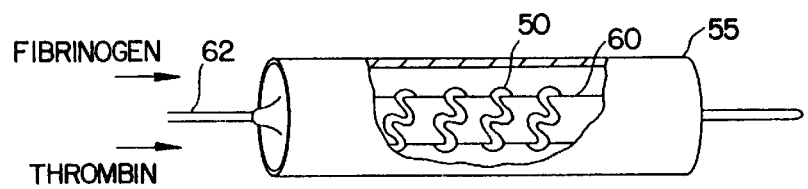
Figure 7:
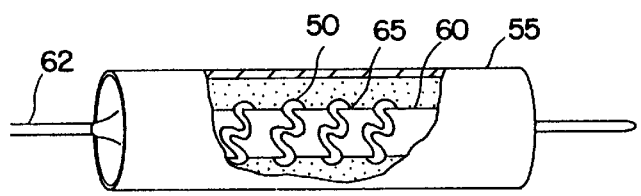
Figure 8:
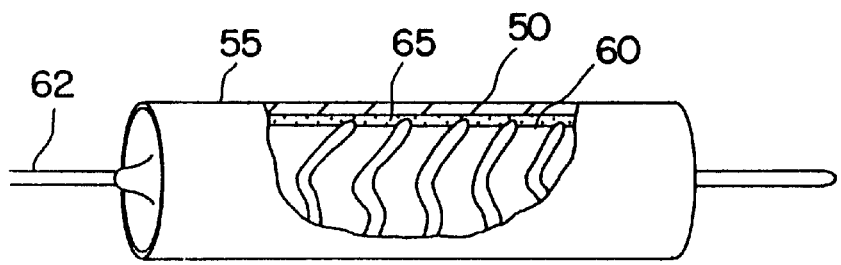
Figure 9:
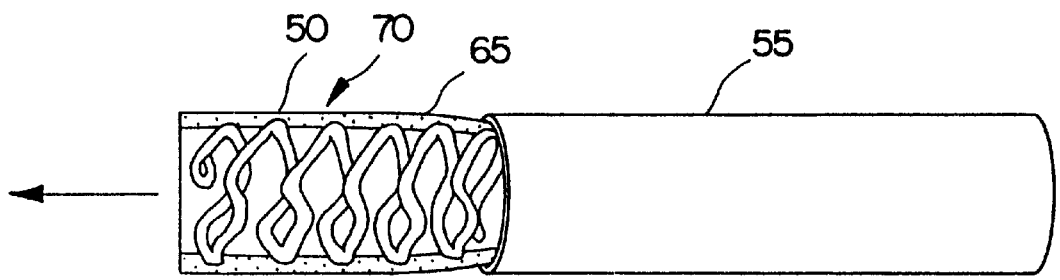
Figure 10:
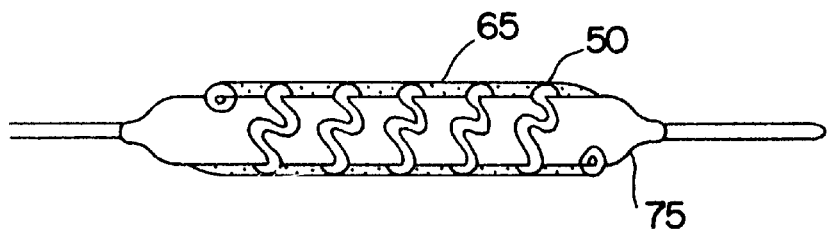

Also, for example, a self-expanding stent of resilient polymeric material such as that disclosed in published international patent application WO 91/12779 "Intraluminal Drug Eluting Prosthesis" could be used in which fibrin is coated onto the stent or incorporated within the polymeric material of the stent. A stent of this general configuration is shown in FIG. 3. The stent 40 has a first set of filaments 42 which are helically wound in one direction and a second set of filaments 44 which are helically wound in a second direction. Any or all of these filaments 42, 44 could be fibrin and/or a blend of fibrin with another polymer. The combination of fibrin with another polymer may be preferred to provide improved mechanical properties and manufacturability for the individual filaments 42, 44. A suitable material for fibrin-containing filaments 42, 44 is the crosslinked blend of polyurethane and fibrin used as a vascular graft material in the article by Soldani et al., "Bioartificial Polymeric Materials Obtained from Blends of Synthetic Polymers with Fibrin and Collagen" International Journal of Artificial Organs, Vol. 14, No. 5, 1991, which is incorporated herein by reference. Other biostable or bioerodeable polymers could also be used. A fibrin-containing stent of this configuration can be affixed to the distal end of a catheter in a longitudinally stretched condition which causes the stent to decrease in diameter. The stent is then delivered through the body lumen on the catheter to the treatment site where the stent is released from the catheter to allow it to expand into contact with the lumen wall. It will be apparent to those skilled in the art that other self-expanding stent designs (such as resilient metal stent designs) could also be used with fibrin either incorporated in the material of the underlying structure of the stent or coated on the underlying structure of the stent.

A preferred method of making a stent according to the present invention is as set forth in FIGS. 4–10. A stent 50 of the type disclosed in U.S. Pat. No. 4,886,062 issued to Wiktor is inserted into a tube 55 which is preferably made from a rigid material and which has an inside diameter which is large enough to accommodate an unexpanded PTCA balloon but which is smaller than a fully inflated PTCA balloon. A PTCA balloon 60 attached to a catheter 62 and inflation device (not shown) is inserted into the stent 50 and tube 55. Fibrinogen at a pH of about 6.5, suspended in a saline solution, and thrombin are inserted into the tube 55 around the deflated balloon 60 and stent 50. The amount of thrombin added is not critical but preferably will polymerize the fibrinogen to fibrin 65 in about 5 minutes. After polymerization, the fibrin is allowed to crosslink for about an hour. The-balloon 60 is then inflated to compress the fibrin 65 between the balloon 60 and tube 55. The balloon 60 is then deflated and removed from the tube 55. The resulting fibrin stent 70 includes the stent 50 embedded in a very thin elastic film of fibrin 65. The fibrin stent 70 may then be removed from the tube 55 and washed in a buffered saline solution. Further processing of the fibrin stent can also be undertaken to neutralize thrombin with PPACK or hirudin; to add anticoagulants such as heparin; to further facilitate crosslinking by incubation at body temperature in a biological buffer such as a solution of blood serum buffered by 4-(2-Hydroxyethyl)-1-piperazineethanesulfonic acid (HEPES); or to add plasticizers such as glycerol. The resulting fibrin stent can then be placed over a balloon, and secured onto the balloon by crimping. The stent can then be delivered transluminally and expanded into place in the body lumen by conventional procedures.

In a variant of this procedure, the metal stent portion may be eliminated to make a fibrin tube which can be placed on a balloon catheter and expanded into place in a body lumen. The absence of permanently implanted metal elements would allow the entire stent to biodegrade as healing is completed in the body lumen.

It will be appreciated by those skilled in the art that while the invention has been described above in connection with particular embodiments the invention is not necessarily so limited and that numerous other embodiments, uses, modifications and departures from the embodiments, and uses may be made without departing from the inventive concepts.

I claim:

1. A device for transluminal treatment of a body lumen comprising:
    a. a catheter;
    b. a stent mounted onto the catheter, the stent having a metal framework and a polymeric preform comprising a thin film of compressed fibrin attached to the metal framework such that the stent and the preform may be inserted into the body lumen on the catheter and expanded into contact with the body lumen with the fibrin retained against the body lumen.

2. The device of claim 1 wherein the preform is comprised of fibrin in which a coagulating protein has been neutralized.

3. The device of claim 1 wherein the metal framework is made from a deformable material.

4. The device of claim 1 wherein the catheter has a balloon at a distal end and the stent affixed to the balloon.

5. The device of claim 1 wherein the preform includes fibrin intermixed with a polymeric material.

6. The device of claim 1 wherein the metal framework is embedded in the preform.

7. The device of claim 1 wherein the preform is a coating on the metal framework.

8. The device of claim 1 wherein the preform also includes a therapeutic substance.

9. The device of claim 8 wherein the therapeutic substance is incorporated into microcapsules.

10. The device of claim 8 wherein the therapeutic substance is selected from the group consisting of anticoagulant drugs, antiplatelet drugs, antimetabolite drugs and antimitotic drugs.

11. The device of claim 10 wherein the therapeutic substance is heparin.

12. A device for transluminal treatment of a body lumen comprising:
   a. a catheter;
   b. a stent mounted onto the catheter, the stent having a framework including a polymeric material and fibrin incorporated within the polymeric material such that the stent and the incorporated fibrin may be inserted into the body lumen on the catheter and expanded into contact with the body lumen with the polymeric material with incorporated fibrin retained against the body lumen.

13. The device of claim 12 wherein the incorporated fibrin is comprised of fibrin in which a coagulating protein has been neutralized.

14. The device of claim 12 wherein the polymeric material is a resilient polymeric material.

15. The device of claim 12 wherein the catheter has a balloon at a distal end and the stent affixed to the balloon.

16. The device of claim 12 wherein the polymeric material with incorporated fibrin also includes a therapeutic substance.

17. The device of claim 16 wherein the therapeutic substance is incorporated into microcapsules.

18. The device of claim 16 wherein the therapeutic substance is selected from the group consisting of anticoagulant drugs, antiplatelet drugs, antimetabolite drugs and antimitotic drugs.

19. The device of claim 18 wherein the therapeutic substance is heparin.

20. A method for preventing restenosis in a body lumen treated to open a luminal restriction, the method comprising the steps of:

providing a catheter and a stent mounted thereon, the stent having a polymeric preform comprising a compressed film of fibrin attached thereto;

advancing the catheter and stent transluminally to the portion of the body lumen having been treated to open the luminal restriction such that the fibrin film is retained on the stent;

radially expanding the stent and fibrin film into contact with the lumen such that the fibrin is retained against the lumen by the stent;

removing the catheter from the body lumen.

21. The method of claim 20 wherein the fibrin also includes a therapeutic substance.

22. The method of claim 21 wherein the therapeutic substance is incorporated in microcapsules.

23. The method of claim 21 wherein the therapeutic substance is selected from the group consisting of anticoagulant drugs, antiplatelet drugs, antimetabolite drugs and antimitotic drugs.

24. The method of claim 23 wherein the therapeutic substance is heparin.

25. A method for preventing restenosis in a body lumen treated to open a luminal restriction, the method comprising the steps of:

providing a catheter and a stent mounted thereon, the stent having a polymeric material and fibrin incorporated within the polymeric material attached thereto;

advancing the catheter and stent transluminally to the portion of the body lumen having been treated to open the luminal restriction such that the polymeric material and incorporated fibrin are retained on the stent;

radially expanding the stent and the polymeric material and incorporated fibrin into contact with the lumen such that the polymeric material and incorporated fibrin are retained against the lumen by the stent;

removing the catheter from the body lumen.

26. The method of claim 25 wherein the fibrin also includes a therapeutic substance.

27. The method of claim 26 wherein the therapeutic substance is incorporated in microcapsules.

28. The method of claim 26 wherein the therapeutic substance is selected from the group consisting of anticoagulant drugs, antiplatelet drugs, antimetabolite drugs and antimitotic drugs.

29. The method of claim 28 wherein the therapeutic substance is heparin.

* * * * *